US011186683B2

United States Patent
Raghuraman et al.

(10) Patent No.: US 11,186,683 B2
(45) Date of Patent: *Nov. 30, 2021

(54) PROCESS OF MANUFACTURING SURFACTANTS AND LUBRICANTS

(71) Applicants: Dow Global Technologies LLC, Midland, MI (US); Northwestern University, Evanston, IL (US)

(72) Inventors: Arjun Raghuraman, Pearland, TX (US); William H. Heath, Lake Jackson, TX (US); Bruce D. Hook, Lake Jackson, TX (US); Wanglin Yu, Pearland, TX (US); Sukrit Mukhopadhyay, Midland, MI (US); Heather A. Spinney, Midland, MI (US); David R. Wilson, Midland, MI (US); Justin M. Notestein, Evanston, IL (US); SonBinh T. Nguyen, Evanston, IL (US)

(73) Assignees: Dow Global Technologies LLC, Midland, MI (US); Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/645,982

(22) PCT Filed: Sep. 14, 2018

(86) PCT No.: PCT/US2018/051002
§ 371 (c)(1),
(2) Date: Mar. 10, 2020

(87) PCT Pub. No.: WO2019/055741
PCT Pub. Date: Mar. 21, 2019

(65) Prior Publication Data
US 2020/0199294 A1    Jun. 25, 2020

Related U.S. Application Data

(60) Provisional application No. 62/635,631, filed on Feb. 27, 2018, provisional application No. 62/558,422, (Continued)

(51) Int. Cl.
*C08G 65/26*      (2006.01)
*B01J 31/02*      (2006.01)
(Continued)

(52) U.S. Cl.
CPC ...... *C08G 65/2609* (2013.01); *B01J 31/0275* (2013.01); *B01J 31/143* (2013.01);
(Continued)

(58) Field of Classification Search
CPC .............. C08G 65/2609; C08G 65/266; C08G 18/4841; C08G 65/2669; C08G 65/2654;
(Continued)

(56) References Cited

U.S. PATENT DOCUMENTS 6,531,566 B1    3/2003   Satake
6,624,321 B2    9/2003   Denninger et al.
(Continued)

FOREIGN PATENT DOCUMENTS

EP        1340780 B1    7/2010
WO    2002057209      7/2002
(Continued)

OTHER PUBLICATIONS

PCT/US2018/051002, International Search Report and Written Opinion dated Nov. 22, 2018.
(Continued)

*Primary Examiner* — Rosalynd A Keys

(57) ABSTRACT

A method of producing an alcohol ethoxylate surfactant or lubricant includes reacting a low molecular weight initiator
(Continued)

with ethylene oxide in the presence of a polymerization catalyst, the low molecular weight initiator having a nominal hydroxyl functionality at least 1, and the polymerization catalyst being a Lewis acid catalyst having the general formula $M(R^1)1(R^2)1(R^3)1(R^4)_{0\ or\ 1}$, whereas M is boron, aluminum, indium, bismuth or erbium, $R^1$, $R^2$ and $R^3$ each includes a same fluoroalkyl-substituted phenyl group, and optional $R^4$ includes a functional group or functional polymer group. $R^1$, $R^2$, and $R^3$ are the same fluoroalkyl-substituted phenyl group. The method further includes forming the alcohol ethoxylate surfactant or lubricant having a number average molecular weight of greater than the number average molecular weight of the low molecular weight initiator in the presence of the Lewis acid catalyst.

7 Claims, 1 Drawing Sheet

Related U.S. Application Data filed on Sep. 14, 2017, provisional application No. 62/558,409, filed on Sep. 14, 2017.

(51) Int. Cl.
   *C08G 18/48* (2006.01)
   *B01J 31/14* (2006.01)
   *C07C 41/03* (2006.01)

(52) U.S. Cl.
   CPC ....... *C08G 18/4841* (2013.01); *C08G 65/266* (2013.01); *C08G 65/2654* (2013.01); *C08G 65/2669* (2013.01); *C08G 65/2684* (2013.01); *B01J 2231/20* (2013.01); *B01J 2531/004* (2013.01); *C07C 41/03* (2013.01)

(58) Field of Classification Search
   CPC ............ C08G 18/4833; C08G 65/2684; B01J 31/0275; B01J 2231/20; B01J 2531/004; C10M 105/18; C10M 2207/046
   See application file for complete search history.

(56) References Cited

U.S. PATENT DOCUMENTS

| | | | |
|---|---|---|---|
| 9,040,657 | B2 | 5/2015 | Laitar et al. |
| 9,388,271 | B2 | 7/2016 | Nakaminami et al. |
| 2002/0128521 | A1* | 9/2002 | Priou ...................... C07C 41/03 568/620 |
| 2011/0230581 | A1 | 9/2011 | Klescewski et al. |
| 2021/0070920 | A1* | 3/2021 | Raghuraman ........ B01J 31/0275 |

FOREIGN PATENT DOCUMENTS

| | | |
|---|---|---|
| WO | 2008123323 | 10/2008 |
| WO | 2016064698 | 4/2016 |

OTHER PUBLICATIONS

PCT/US2018/051002, International Preliminary Report on Patentability dated Mar. 17, 2020.

\* cited by examiner

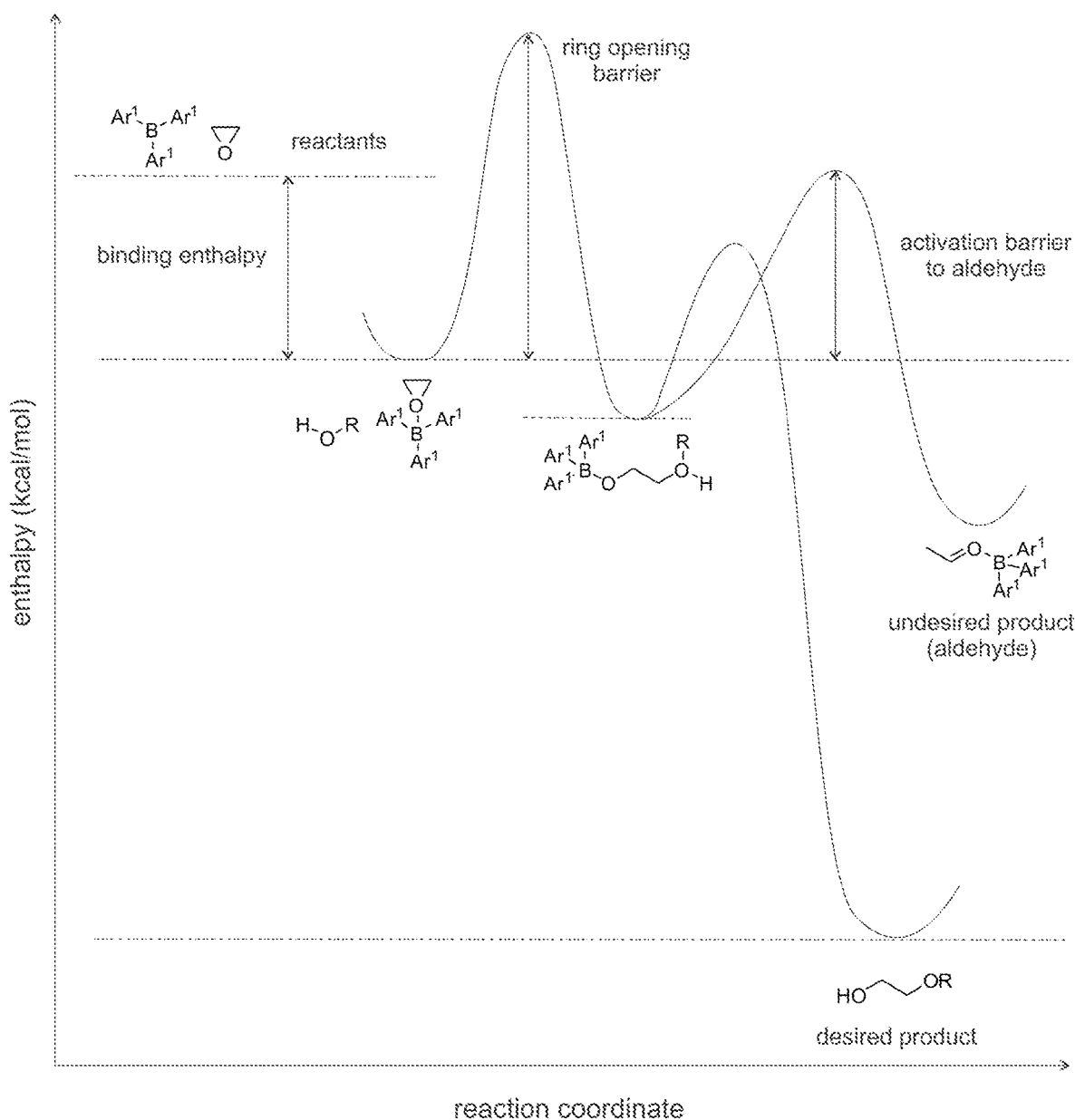

PROCESS OF MANUFACTURING SURFACTANTS AND LUBRICANTS

FIELD

Embodiments relate to methods of manufacturing alcohol ethoxylate surfactants and lubricants using at least a Lewis acid catalyst, alcohol ethoxylate surfactants and lubricants prepared using at least the Lewis acid catalyst, and/or products/compositions that include the alcohol ethoxylate surfactants and lubricants prepared using at least the Lewis acid catalyst.

INTRODUCTION

Polyether alcohols (i.e., polyols and monols) are produced by polymerizing an alkylene oxide in the presence of a starter compound (also referred to as an initiator) and a catalyst. The starter compound has one or more functional groups the alkylene oxide can react with to begin forming polymer chains. The starter compound may influence the molecular weight and establish the number of hydroxyl groups that the resultant polyether alcohol will have. Polyethers alcohols such as alcohol ethoxylates may be useful as, e.g., surfactants and lubricants.

Alcohol ethoxylates may be produced, e.g., by polymerizing at least ethylene oxide in the presence of a starter compound that is a $C_6$-$C_{24}$ alcohol or a mixture of such alcohols and a catalyst. Various catalysts and process technologies have been developed to make commercially valuable polyether alcohols, such as alcohol ethoxylate products.

With respect to the catalyst for forming polyether alcohols, manufacturing is moving toward the use of a double-metal cyanide (DMC) catalyst in place of an alkali metal catalyst (such as a KOH based catalyst). A disadvantage of DMC catalysts is that they are unable to efficiently polymerize ethylene oxide onto starter compounds, as taught in U.S. Pat. No. 7,645,717. A further disadvantage of DMC catalysts is that they may activate slowly, as is taught in U.S. Pat. No. 9,040,657. In particular, preparation of polyether polyols using the DMC catalyst may begin with a stage of the reaction known as the catalyst induction period. During this stage of the reaction, the DMC catalyst is believed to become converted in situ from an inactive form into a highly active form that rapidly polymerizes the alkylene oxide as long as the catalyst remains active. This catalyst induction period is typically an indeterminate period of time following the first introduction of alkylene oxide to the reactor. It is common to introduce a small amount of alkylene oxide at the start of the polymerization process and then wait until the catalyst has become activated (as indicated, e.g., by a drop in reactor pressure due to the consumption of the initial alkylene oxide that had been charged into the reactor) before continuing with the alkylene oxide feed. Very little or no polymerization occurs until the catalyst has become activated, such that long activation times have a direct negative impact on the productivity of the process. It is sometimes the case that the catalyst does not become activated at all. Such a failure of the catalyst to activate may result in the abandonment of the attempt, and the process is started over again from the beginning. As such, the activation process results in some loss of productivity under the best circumstances, and under the worst circumstances can cause a loss of the entire batch of starting mixture. Thus, the reduction or elimination of the induction period at the start of the alkoxylation reaction is seen to be highly desirable.

Currently, base-catalyzed polymerization (e.g., KOH polymerization) is the most commonly used ethoxylation process for alcohols. One problem often seen in ethoxylating alcohols to make surfactant and lubricant products is low conversion of the alcohol starter compound. Insufficient alcohol conversion results in undesirable high unreacted alcohol residue left in the final product. Alcohol residue in the final product may cause odor problem, may negatively impact the performance of product, and/or in extreme situations, may render the final product not useful. Low alcohol starter conversion may become more problematic when a hindered alcohol is used as the starter compound. Examples of hindered alcohols include branched primary alcohols and linear or branched secondary alcohols. Secondary alcohols are particularly challenging to make into quality alcohol ethoxylate surfactant and lubricant products.

Secondary alcohol ethoxylates may be useful as high performance nonionic surfactants and lubricants, e.g., in multiple application areas. Due to the relatively lower reactivity of the hydroxyl groups in a secondary alcohol vs. primary hydroxyl group that is generated from ethylene oxide ring opening during the polymerization, quality secondary alcohol ethoxylate products typically cannot be manufactured by using a base-catalyzed ethoxylation process. When a base-catalyzed ethoxylation process is used for manufacturing a secondary alcohol, large portions of the starter compound may undesirably remain unreacted and the resultant ethoxylated product may have a broad molecular weight distribution (e.g., based on high molecular ethoxylate components). Different from linear or branched primary alcohol ethoxylates, currently secondary alcohol ethoxylate products are commercially produced by using a two-step ethoxylation process, in which a secondary alcohol starter compound is first reacted with a small amount of ethylene oxide in the presence of a Lewis acid catalyst, e.g. boron trifluoride, to get a low EO adduct as an intermediate, from which various grades of ethoxylated products are produced through a second base-catalyzed ethoxylation process. The complexity of the two step process may result in high manufacturing cost of secondary alcohol ethoxylates. Accordingly, it is desired that quality secondary alcohol ethoxylate products could be produced through a one-step ethoxylation process.

DMC catalysts have been studied for one-step ethoxylation processes to make secondary alcohol ethoxylate surfactants (e.g., see International Publication No. WO 2012/071149). While the DMC catalyst can significantly increase alcohol starter conversion, the alcohol conversion rate by DMC may still not be sufficient to produce commercially viable secondary alcohol ethoxylate surfactants. In addition, DMC tends to generate high molecular polyethylene glycol by-products that cause hazy or precipitation problem in either the final product and/or a formulated system that includes the final product.

The disadvantages of the use of conventional Lewis acid catalyst such as boron trifluoride alone to polymerize epoxides is well-known, e.g., as taught in U.S. Pat. No. 6,624,321. The Lewis acids may significantly increase hindered alcohol starter conversion when compared to conventional base catalysts. However, a drawback associated with boron triflouride as an ethoxylation catalyst is the formation of dioxane. It is believed that the dioxane is formed by degradation of polyethylene oxide via oxonium salts, which also limits the attainable molecular weight of ethoxylation product. Certain Lewis acids, such as boron trifluoride, may be sensitive to the structure of alcohol starter compounds which may result in catalyst decomposition and release of a highly corrosive HF side-product and incorporation of fluorine atoms in the backbone of the polymerization product. This may require high levels of catalyst loading which ultimately require the need for a later process stage to remove catalyst from the resultant product. Further, boron trifluoride is regarded as hazardous material that is also moisture sensitive and difficult to handle.

The use of tris(pentafluorophenyl)borane catalyst during ring-opening polymerization of an alkylene oxide is taught, e.g., in U.S. Pat. No. 6,531,566. The tris(pentafluorophenyl) borane catalyst provides several advantages over conventional Lewis acids such as boron trifluoride. For example, the pentafluorophenylborane catalyst is not corrosive, easy to handle, and appreciably more active. However, pentafluorophenylborane catalyst produces an undesirable side-reaction leading to formation of aldehydes and acetal linkages in the polyol backbone.

The use of a dual catalyst package for producing a polyol having a high primary hydroxyl group content, which includes a DMC catalyst and a Lewis acid catalyst such as tris(pentafluorophenyl)borane is disclosed, e.g., in International Publication No. WO 2016/064698. The DMC catalyst enables the production of high molecular weight segments efficiently and the Lewis acid catalyst enables the formation of primary hydroxyl end groups. This method may minimize the residence time of the Lewis acid step and therefore the amount of side-product.

A method of using a combination of DMC and KOH catalysts to produce EO-capped polyether polyols is taught, e.g., in U.S. Patent Publication No. 2011/0230581. In this process, the DMC catalyst is utilized to polymerize propylene oxide (PO) and KOH catalyst is utilized to promote ethylene oxide (EO) capping. This technology suffers from all the drawbacks of conventional KOH technology, such as slow kinetics and need for catalyst removal or finishing steps in the resultant polyether polyols.

A method of using a combination of tris(pentafluorophenyl)borane (Lewis acid) and KOH catalysts to product EO-capped polyether polyols is taught in, e.g., U.S. Pat. No. 9,388,271. In this process, the tris(pentafluorophenyl)borane catalyst is utilized to polymerize PO in a first step. During the first step, the vapor phase in the autoclave is circulated through a reaction column and distillation column and back to the autoclave reactor in order to minimize side-product formation. In a second step, the KOH catalyst is utilized to polymerize EO onto the PO chain ends. This process is complicated and may require finishing step(s) to remove KOH catalyst residues.

In addition, many polyethers are block copolymers of propylene oxide and ethylene oxide, or 1,2-butylene oxide and ethylene oxide. In such cases, when alkaline hydroxide or DMC catalysts are used, the terminal hydroxide for the polypropylene oxide block, or the polybutylene oxide block, is a secondary alcohol. Just as in the ethoxylation of secondary alcohol initiators, alkaline hydroxide, and DMC catalysts do not provide balanced ethoxylation of the polyol polyether since once a primary alcohol is created from the initial conversion of the polyol polyether, these catalysts have more selectivity to further ethoxylate the already ethoxylated molecules over the unethoxylated molecules. This creates broad dispersity in the amount of ethoxylation on the polyol polyethers, even to the point of some fraction of the polyol polyether having no ethoxylation at all.

Therefore, improvements are sought with respect to producing an alcohol ethoxylates surfactant or lubricant (such as a secondary alcohol ethoxylate surfactant or lubricant) efficiently in such a way so as to not require a catalyst removal step and/or to changing the selectivity of the Lewis acid catalyst itself, e.g., to improve yield of the desired ethylene oxide-based polyether alcohol product. Further, improvements are sought with respect to a catalyst that can perform a one-step ethoxylation process on a hindered alcohol, e.g., a secondary alcohol, to produce useful alcohol ethoxylate surfactants, while minimizing and/or avoiding problems with the current process technologies as described above. Also, improvements are sought with respect to a catalyst that can perform a one-catalyst alkoxylation with propylene oxide and/or butylene oxide to form polymer intermediates followed by ethoxylation of the polymer intermediates (e.g., where the polymer intermediates is a hindered alcohol such as a secondary alcohol), to produce useful alcohol ethoxylate surfactants and lubricants, while minimizing and/or avoiding problems with the current process technologies as described above.

SUMMARY

Embodiments may be realized by providing a method of producing an alcohol ethoxylate surfactant or lubricant, the method includes reacting a low molecular weight initiator with ethylene oxide in the presence of a polymerization catalyst, the low molecular weight initiator having a nominal hydroxyl functionality at least 1, and the polymerization catalyst being a Lewis acid catalyst having the general formula $M(R^1)_1(R^2)_1(R^3)_1(R^4)_{0 \text{ or } 1}$, whereas M is boron, aluminum, indium, bismuth or erbium, $R^1$, $R^2$ and $R^3$ each includes a same fluoroalkyl-substituted phenyl group, and optional $R^4$ includes a functional group or functional polymer group. The method further includes forming the alcohol ethoxylate surfactant or lubricant having a number average molecular weight of greater than the number average molecular weight of the low molecular weight initiator in the presence of the Lewis acid catalyst.

BRIEF DESCRIPTION OF THE DRAWINGS

Features of the embodiments will become more apparent to those of ordinary skill in the art by describing in detail exemplary embodiments thereof with reference to the attached drawings in which:

FIG. 1 illustrates an exemplary diagram of reaction coordinate to enthalpy for aldehyde formation.

DETAILED DESCRIPTION

Ethylene oxide (EO) is an important and widely used monomer in the production of alcohol ethoxylate surfactants and lubricants. EO polymerization offers the opportunity to significantly increase the hydrophilicity and reactivity of the alcohol by virtue of the resulting primary hydroxyl end groups. Homopolymers of EO such as certain polyethylene glycols, may find limited use in certain applications as they may crystallize readily and/or have a high affinity to water. The high affinity of polyethylene glycols to water may be detrimental to the properties of resultant products, e.g., as the products may be sensitive to the humidity in the environment. The use of block structures formed by the addition of short EO segments (referred to as EO capping) to PO alcohols has been proposed as a possible way to minimize difficulties associated with processability and water affinity. Another approach is to copolymerize EO and PO (e.g., mixed feed alcohols) to form alcohols that are composed of statistical mixtures of EO and PO.

Currently, alcohol ethoxylates are typically produced on an industrial scale utilizing KOH-catalyzed polymerization technology. Also, many have found that DMC catalysts are typically unable to efficiently polymerize EO at a commercial scale. The use of conventional Lewis acids to polymerize EO is not preferred due to side-reactions. For example, these side-reaction may result in volatile side-products such as small cyclic ethers and acetaldehyde. As a result the yield of the reaction may be greatly diminished. In addition, extra purification steps may be needed to obtain a product of sufficiently high quality. By yield it is meant herein percent yield, which is well-known as determined according to the following equation:

% yield=(actual yield)/(theoretical yield)×100

As is well-known, the actual yield and theoretical yield may be based on weight percent or mole percent. The actual % yield is a dimensionless number.

Further, as discussed in International Publication No. WO 2012/091968, certain Lewis acids that may essentially require no activation time have been evaluated as polymerization catalysts. However, some Lewis acids may become deactivated rapidly and may not be capable of producing high molecular weight polymers or of obtaining high conversions of alkylene oxides to polymer. Further, high amounts of alkaline catalysts, such as sodium hydroxide may require treatment such as filtration and/or acid finishing/neutralization (e.g., as discussed in U.S. Pat. No. 5,468,839) to reduce the base content of the resultant product. The use of a sufficiently low amount of Lewis acid catalysts and optionally a DMC catalyst may eliminate the need for such treatment, while also providing for control and/or selectivity. However, certain Lewis acids may promote undesirable side reactions. The presence of certain side products in an alcohol product may necessitate performing an additional finishing step on the resultant product.

Accordingly, embodiments relate to certain Lewis acid catalysts, and processes using such Lewis acid catalysts, that may provide advantages with respect to minimizing side reactions such as those that produce undesired by-products and decrease yield of the desired products, while still allowing for precise control of the polymerization reaction. By Lewis acid it is meant a substance that can accept a pair of electrons. In other words, a Lewis acid in an electron-pair acceptor.

Embodiments may relate to providing alcohol ethoxylates having a desirable high yield, e.g., of EO capped polyether alcohols and/or polyether alcohols prepared using a mixed feed of EO and another alkylene oxide. By EO capped alcohol it is meant polyether alcohols chains that have the addition of ethylene oxide (e.g., ethylene oxide only and essentially excluding intended addition of any other alkylene oxides such as propylene oxide and 1,2-butylene oxide) on at least one end of such chain. EO capping may be performed on a polyether alcohol (e.g., derived from propylene oxide, ethylene oxide, and/or 1,2-butylene oxide). EO capping may result in an alcohol product having a high primary hydroxyl content (e.g., at least 30%, at least 40%, at least 50%, at least 60%, at least 70%, at least 80%, etc.) For a mixed feed process, copolymerization EO and another alkylene oxide such as propylene oxide may be performed on a starter compound and may result in an alcohol product having a higher primary hydroxyl content than that prepared with a feed of propylene oxide alone.

During the polymerization process to form a polyether polyol, some Lewis acid catalysts such as the tris(pentafluorophenyl)borane catalyst, may have a disadvantage in that certain side reactions may occur at undesirable levels (depending on the outcome desired). An example of such side reactions is the tris(pentafluorophenyl)borane catalyst-assisted formation of acetaldehyde as shown below in Schematic 1, which may occur in the presence of alcohols and may lead to the lack of desired chemoselectivity for the resultant polyether polyol. Further, high amount of formation of acetaldehyde or other volatile side-products may result in poor yield.

Schematic 1

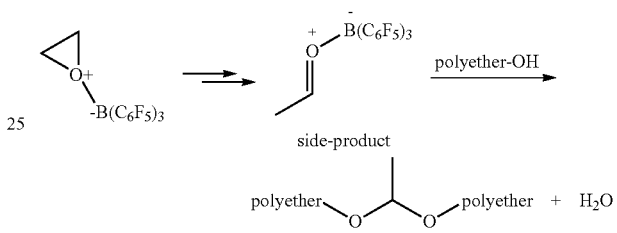

Further, a subsequent acetaldehyde-alcohol coupling reaction to form an acetal linkage, may result in higher molecular weight species, such as dimers, as compared to when the coupling is not present and/or may make molecular weight control challenging especially at a commercial scale. Also, the water byproduct that results from the coupling reaction could potentially consume monomer and result in the formation of diols and/or alter the catalytic activity of the tris(pentafluorophenyl)borane catalyst.

Accordingly, in exemplary embodiments, a reaction system for forming a polyether alcohol (such as an ethylene oxide based alcohol) uses a Lewis acid catalyst (e.g., in a low amount such that filtration and acid finishing/neutralization are not required for the resultant polyether alcohol) that minimizes side reactions and optionally may be combined with a DMC catalyst. For example, it is proposed to use triarylborane catalysts that have fluoroalkyl-substituted phenyl groups, which may allow for improvements with respect to selectively minimizing side reactions so as to improve yield of desired EO based products and/or for precise control of the polymerization reaction (such as an EO-capping reaction).

In particular, it has been found that triarylborane catalysts containing fluoroalkyl substituents may significantly decrease the side-reactions leading to lower acetal linkages in the backbone. It is believed that the fluoroalkyl groups may impart unique properties to the metal (such as boron) active center. For example, the Hammett constant ($\sigma$) for a fluorine group in the para position $\sigma_p$=0.06 whereas that for a $CF_3$ group in the para position is 0.54. As such, a $CF_3$ group may act as a unique electron withdrawing group, which is in part related to the inability of F atoms to donate into the ring.

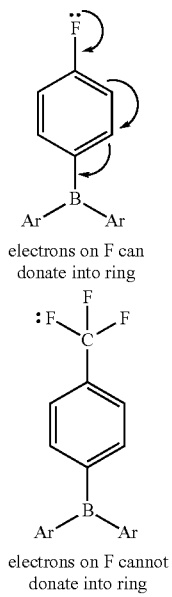

electrons on F can donate into ring electrons on F cannot donate into ring

Embodiments relate to forming a polyether alcohol (e.g., an ethylene oxide based alcohol) with a high yield and low amount of unreacted starter compound. The polyether alcohol may have a low degree of ethoxylation. By degree of ethoxylation it is meant moles of EO per mole of starter. For example, the polyether alcohol may have a degree of ethoxylation that is less than 12 moles, greater than 2 moles, greater than 3 moles, greater than 5 moles, etc of EO per mole of starter. The polyether alcohol may have a relatively high number average molecular weight (i.e., greater than 500 g/mol, greater than 1000 g/mol, greater than 2,500 g/mol such as from 2,600 g/mol to 12,000 g/mol, 3,000 g/mol to 6,000 g/mol, etc.) The polyether alcohol may have a specified primary hydroxyl group content (e.g., from 30% to 90%, based on a total number of hydroxyl groups). For example, the Lewis acid catalyst may be used to enable a desired amount of ethylene oxide capping for the resultant polyether alcohol as a means toward achieving a desired primary hydroxyl group content. Certain primary hydroxyl content values may be sought after for specific end use applications.

According to exemplary embodiments, a catalyst component for forming the polyether alcohol may utilize the Lewis acid catalyst and optionally the DMC catalyst. For example, the Lewis acid catalyst may be used without the DMC catalyst, or the DMC catalyst and the Lewis acid catalyst may be simultaneously or sequential added. For example, in a DMC-Lewis acid dual catalyst system, a polymerization method may include initially adding a DMC catalyst and later adding the Lewis acid catalyst that is separately provided and allowed to react at a lower temperature than the temperature at which the DMC catalyst was added. The Lewis acid catalyst may be active at a lower temperature range (e.g., from 60° C. to 115° C.) than a temperature range at which the DMC catalyst may be active (e.g., from 125° C. to 160° C.).

Polyether alcohols include polyols that have multiple ether bonds. Exemplary polyether alcohols include polyether hybrid alcohols (such as polyether carbonate alcohols and polyether ester alcohols). The polyether alcohols are produced by polymerizing an alkylene oxide component that includes at least one alkylene oxide and an initiator component that includes at least one initiator compound (i.e., starter compound). The initiator compound has one or more functional groups at which the alkylene oxide can react to begin forming the polymer chains. The main functions of the initiator compound are to provide hydrophobicity and surface activity, molecular weight control and to establish the number of hydroxyl groups that the monol or polyol product will have. The polyether carbonate may be produced by polymerizing carbon dioxide, at least one alkylene oxide, and an initiator compound. The polyether ester may be produced by polymerizing at least one alkylene oxide with a carboxylic acid initiator.

Lewis Acid Catalyst

According to exemplary embodiments, the Lewis acid catalyst has the general formula $M(R^1)_1(R^2)_1(R^3)_1(R^4)_{0\ or\ 1}$, whereas M is boron, aluminum, indium, bismuth or erbium, $R^1$, $R^2$, and $R^3$ are each a fluoroalkyl-substituted phenyl group, and optional $R^4$ is a functional group or functional polymer group. The M in the general formula may exist as a metal salt ion or as an integrally bonded part of the formula. $R^1$, $R^2$, and $R^3$ are each a fluoroalkyl-substituted phenyl group. $R^1$, $R^2$, and $R^3$ are each the same fluoroalkyl-substituted phenyl group.

$R^1$, $R^2$, and $R^3$ may include the fluoroalkyl-substituted phenyl group or may consist essentially of the fluoroalkyl-substituted phenyl group. Similarly, $R^4$ may include the functional group or functional polymer group, or consist essentially of the $R^4$ functional group or functional polymer group.

With respect to $R^1$, $R^2$, and $R^3$, by fluoroalkyl-substituted phenyl group it is meant a phenyl group that includes at least one hydrogen atom replaced with a fluoroalkyl group, which is an alkyl group with at least one hydrogen atom replaced with a fluorine atom. For example, the fluoroalkyl group may have the structure $C_nH_mF_{2n+1-m}$, whereas n is greater than or equal to 1 and less than or equal to 5. Also, m is a number that reflects a balance of the electrical charges to provide an overall electrostatically neutral compound, e.g., can be zero, one or greater than one. The phenyl group of the fluoroalkyl-substituted phenyl may be substituted to include other groups in addition to the at least one fluoroalkyl group, e.g., a fluorine atom and/or chlorine atom that replaces at least one hydrogen of the phenyl group. For example, $R^1$, $R^2$, and $R^3$ may be a fluoro/chloro-fluoroalkyl-substituted phenyl group (meaning one fluoro or chloro group and at least one fluoroalkyl group are substituted on the phenyl group), difluoro/chloro-fluoroalkyl-substituted phenyl group (meaning two fluoro, two chloro, or a fluoro and chloro group and at least one fluoroalkyl group are substituted on the phenyl group), trifluoro/chloro-fluoroalkyl-substituted phenyl group (meaning three fluoro, three chloro, or a combination of fluoro and chloro groups totaling three and at least one fluoroalkyl group are substituted on the phenyl group), or tetrafluoro/chloro-fluoroalkyl-substituted phenyl group (meaning four fluoro, four chloro, or a combination of fluoro and chloro groups totaling four and one fluoroalkyl group are substituted on the phenyl group).

With respect to optional $R^4$, the functional group or functional polymer group may be a Lewis base that forms a complex with the Lewis acid catalyst (e.g., a boron based Lewis acid catalyst) and/or a molecule or moiety that contains at least one electron pair that is available to form a dative bond with a Lewis acid. The Lewis base may be a polymeric Lewis base. By functional group or functional polymer group it is meant a molecule that contains at least one of the following: water, an alcohol, an alkoxy (examples include a linear or branched ether and a cyclic ether), a ketone, an ester, an organosiloxane, an amine, a phosphine, an oxime, and substituted analogs thereof. Each of the alcohol, linear or branched ether, cyclic ether, ketone, ester, alkoxy, organosiloxane, and oxime may include from 2-20 carbon atoms, from 2-12 carbon atoms, from 2-8 carbon atoms, and/or from 3-6 carbon atoms.

For example, the functional group or functional polymer group may have the formula (OYH)n, whereas O is O oxygen, H is hydrogen, Y is H or an alkyl group, and n is an integer (e.g., an integer from 1 to 100). However, other known functional polymer groups combinable with a Lewis acid catalyst such as a boron based Lewis acid catalyst may be used. Exemplary cyclic ethers include tetrahydrofuran and tetrahydropyran. Polymeric Lewis bases are moieties containing two or more Lewis base functional groups such as polyols and polyethers based on polymers of ethylene oxide, propylene oxide, and butylene oxide. Exemplary polymeric Lewis bases include ethylene glycol, ethylene glycol methyl ether, ethylene glycol dimethyl ether, diethylene glycol, diethylene glycol dimethyl ether, triethylene glycol, triethylene glycol dimethyl ether, polyethylene glycol, polypropylene glycol, and polybutylene glycol.

Exemplary Lewis acid catalysts have the following structure in which each of $Ar^1$ includes at least one fluoroalkyl (Y) group substituted on a phenyl group and optionally at least one fluoro or chloro (X) substituted on the phenyl group:

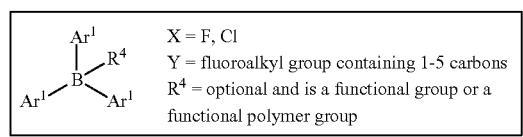

X = F, Cl
Y = fluoroalkyl group containing 1-5 carbons
$R^4$ = optional and is a functional group or a functional polymer group

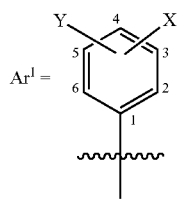

Y can be attached to positions 3, 4 or 5 or a combination of these
X can be attached to positions 2, 3, 4, 5 or 6 or a combination of these Whereas each $Ar^1$ has the same structure. Exemplary structures for $Ar^1$ are the following, referred to as Set 1 structures:

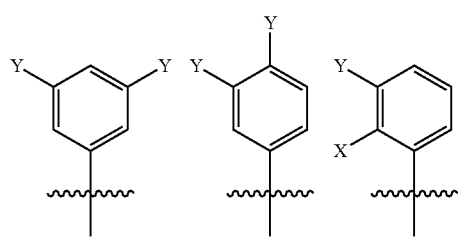

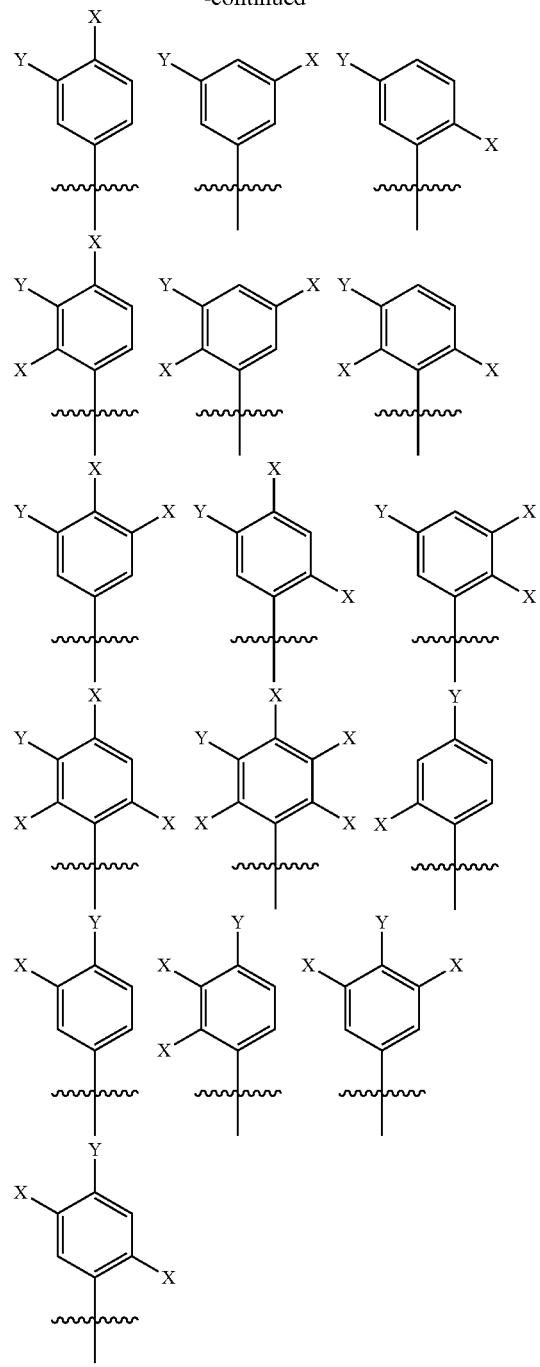

According to exemplary embodiments, the Lewis acid catalyst is a boron based Lewis acid catalyst that has the general formula $B(R^1)_1(R^2)_1(R^3)_1(R^4)_{0 \, or \, 1}$, whereas $R^1$, $R^2$, and $R^3$ are the fluoroalkyl-substituted phenyl group, and optionally $R^4$ is the functional group or functional polymer group. For example, the fluoroalkyl-substituted phenyl group is a 2,4-difluoro-3-(trifluoromethyl)phenyl group. For example, the fluoroalkyl-substituted phenyl group is a 2,4,6-trifluoro-3-(trifluoromethyl)phenyl group. For example, the fluoroalkyl-substituted phenyl group is a 3,5-difluoro-4-(trifluoromethyl)phenyl group. In exemplary embodiments, at least one of $R^1$ or $R^2$ or $R^3$ is a 3,4- or 3,5-bis(fluoroalkyl)-substituted phenyl group (e.g., a 3,4 or 3,5-bis (trifluoromethyl)-substituted phenyl group). For example, $R^4$ is a cyclic ether having 3-10 carbon atoms.

Exemplary structures for the Lewis acid catalysts, where M is Boron are shown below:

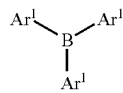

Basic Catalyst Structure
$Ar^1 = R^1, R^2,$ or $R^3$
$Ar^2 = R^1, R^2,$ or $R^3$
$Ar^3 = R^1, R^2,$ or $R^3$
B = Boron Exemplary Structure 1

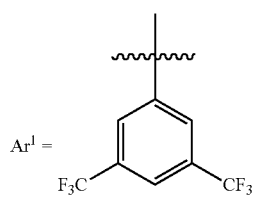

Exemplary Structure 2

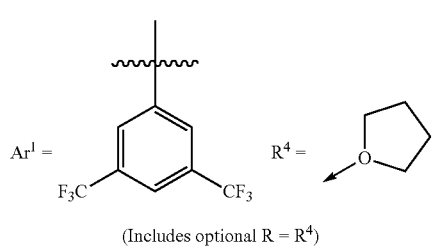

(Includes optional R = $R^4$)

Exemplary Structure 3

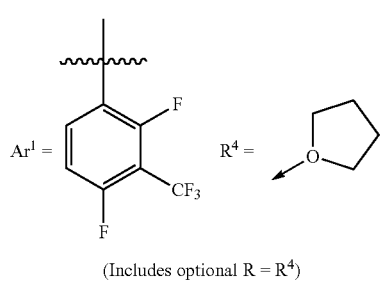

(Includes optional R = $R^4$)

Exemplary Structure 4

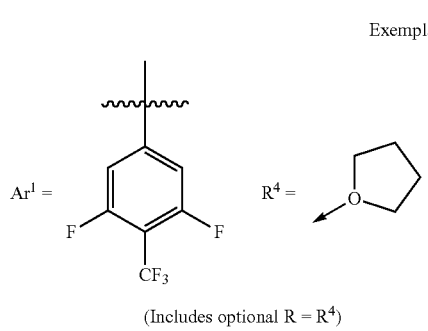

(Includes optional R = $R^4$)

Exemplary Structure 5

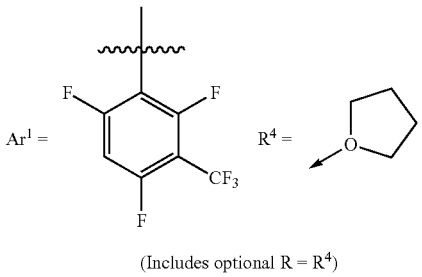

(Includes optional R = $R^4$)

While the above illustrates exemplary structures that include boron, similar structures may be used that include other metals such as aluminum, indium, bismuth, and/or erbium.

Without intending to be bound by this theory, certain $R^4$ may help improve shelf life of the catalyst, e.g., without significantly compromising catalyst activity when utilized in a polymerization reaction. For example, the catalyst comprising M, $R^1$, $R^2$, and $R^3$ may be present in the form with the optional $R^4$ (form $M(R^1)_1(R^2)_1(R^3)_1(R^4)_1$) or without the optional $R^4$ (form $M(R^1)_1(R^2)_1(R^3)_1$). The optional $R^4$ may dissociate step-wise from $M(R^1)_1(R^2)_1(R^3)_1(R^4)$, to give free $M(R^1)_1(R^2)_1(R^3)_1$, as shown below for M=B, which free $M(R^1)_1(R^2)_1(R^3)_1$ may be a catalyst for an alkoxylation/polymerization process, and/or may dissociate from $M(R^1)_1(R^2)_1(R^3)_1(R^4)_1$ in a concerted or other single-step process with the alkylene oxide to give a catalyst for an alkoxylation/polymerization process.

For example, the catalyst including M, $R^1$, $R^2$, and $R^3$ may be present in the form with and without the optional $R^4$ group, as shown below.

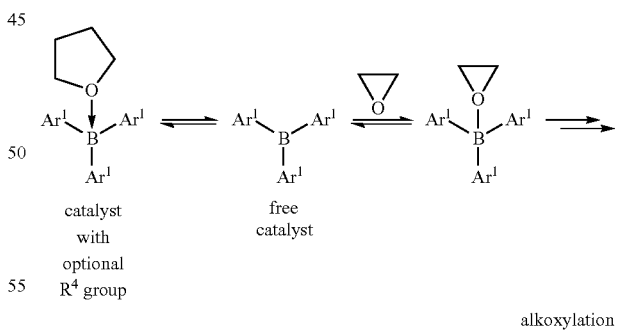

catalyst with optional $R^4$ group free catalyst alkoxylation

The ability of the optional $R^4$ group to protect the boron, aluminum, indium, bismuth and erbium center from inadvertent decomposition reactions may be related to the decrease in the accessible volume of the center. The accessible volume of the center is defined as the volume around the atom, such as boron atom, that is available for interaction with a small molecule like a solvent molecule.

| Catalyst | Accessible volume of boron (%) |
|---|---|
| (structure with F₃C, F, B, CF₃ groups) | 25 |
| (structure with F₃C, F, B, CF₃ groups, O/THF) | 10 |

Suitable R⁴ groups that can help increase catalyst shelf stability, e.g., without compromising catalyst activity, include diethyl ether, cyclopentyl methyl ether, methyl tertiary-butyl ether, tetrahydrofuran, tetrahydropyran, 1,4-dioxane, acetone, methyl isopropyl ketone, isopropyl acetate, and isobutyl acetate.

The Lewis acid catalyst used in exemplary embodiments may be a blend catalyst that includes one or more Lewis acid catalyst (e.g., each having the general formula $B(R^1)_1(R^2)_1(R^3)_1(R^4)_{0 \text{ or } 1}$) and optionally at least one other catalyst (such as catalyst known in the art for producing polyether polyols). The blend catalyst may optionally include other catalysts, in which Lewis acid catalysts having the general formula account for at least 25 wt %, at least 50 wt %, at least 70 wt %, at least 75 wt %, at least 80 wt %, at least 85 wt %, at least 90 wt %, at least 95 wt %, at least 99 wt %, etc., of the total weight of the blend catalyst.

DMC Catalyst

The catalyst component may optionally include DMC catalysts. Exemplary DMC catalysts and method of producing DMC catalyst are described, e.g., in U.S. Pat. Nos. 3,278,457, 3,278,458, 3,278,459, 3,404,109, 3,427,256, 3,427,334, 3,427,335, and 5,470,813. An exemplary type of DMC catalyst is a zinc hexacyanocobaltate catalyst complex. The mDMC catalyst complexes may be prepared using modified methods of forming the DMC catalysts. The DMC catalyst, e.g., ones that are known in the art, may be used in the catalyst system that includes the Lewis acid catalyst. The DMC catalyst may be the first or second catalyst that is provided.

For example, the DMC catalysts may be represented by the Formula 1:

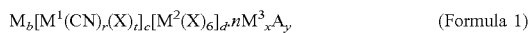

(Formula 1)

wherein M and M³ are each metals; M¹ is a transition metal different from M. X¹ represents a group other than cyanide that coordinates with the M¹ ion. M² is a transition metal. X² represents a group other than cyanide that coordinates with the M² ion. X¹ or X² may each independently be a halogen, sulfate, nitrate, phosphate, carbonate, or chlorate. In exemplary embodiments, X¹ and X² are the same and are chloride. A¹ represents an anion; b, c and d are numbers that reflect an electrostatically neutral complex; r is from 4 to 6; t is from 0 to 2; x and y are integers that balance the charges in the metal salt $M^3_x A_y$, and n is zero or a positive integer. For example, n is from 0.01 to 20. The foregoing formula does not reflect the presence of neutral complexing agents such as t-butanol which are often present in the DMC catalyst complex.

Referring to Formula (I), M and M³ each are a metal ion independently selected from (e.g., from the group consisting of): $Zn^{2+}$, $Fe^{2+}$, $Co^{+2+}$, $Ni^{2+}$, $Mo^{4+}$, $Mo^{6+}$, $Al^{+3+}$, $V^{4+}$, $V^{5+}$, $Sr^{2+}$, $W^{4+}$, $W^{6+}$, $Mn^{2+}$, $Sn^{2+}$, $Sn^{4+}$, $Pb^{2+}$, $Cu^{2+}$, $La^{3+}$ and $Cr^{3+}$. Exemplary embodiments include at least $Zn^{2+}$. Further, M¹ and M² each are a metal ion independently selected from (e.g., from the group consisting of): $Fe^{3+}$, $Fe^{2+}$, $Co^{3+}$, $Co^{2+}$, $Cr^{2+}$, $Cr^{3+}$, $Mn^{2+}$, $Mn^{3+}$, $Ir^{3+}$, $Ni^{2+}$, $Rh^{3+}$, $Ru^{2+}$, $V^{4+}$, $V^{5+}$, $Ni^{2+}$, $Pd^{2+}$, and $Pt^{2+}$. Among the foregoing, those in the plus-three oxidation state may be used for the M¹ and M² metal. Exemplary embodiments include $Co^{+3}$ and/or $Fe^{+3}$.

Suitable anions A include, but are not limited to, halides such as chloride, bromide and iodide, nitrate, sulfate, carbonate, cyanide, oxalate, thiocyanate, isocyanate, perchlorate, isothiocyanate, an alkanesulfonate such as methanesulfonate, an arylenesulfonate such as p-toluenesulfonate, trifluoromethanesulfonate (triflate), and a $C_{1-4}$ carboxylate. Exemplary embodiments include the chloride ion.

Referring to Formula (I), r is an integer that is 4, 5 or 6. In exemplary embodiments, r is 4 or 6. Further, t is an integer from 0 to 2, and in exemplary embodiments t is 0. The sum of r+t may equal six.

In exemplary embodiments, the DMC catalyst is a zinc hexacyanocobaltate catalyst complex. The DMC catalyst may be complexed with t-butanol. The DMC catalyst used in exemplary embodiments may be a blend catalyst that includes of one or more DMC catalysts. The blend catalyst may optionally include a non-DMC catalyst, in which the DMC catalysts account for at least 75 wt % of the total weight of the blend catalyst. The blend catalyst may exclude any of Lewis acid catalyst that is added at a later time in the dual catalyst system.

Use of the Catalyst Component

In embodiments where the Lewis acid catalyst is used the alkoxylation of low hydroxyl equivalent weight starter compounds, also referred to as initiators, may proceed directly from the starter compound to a finished polyether alcohol by the polymerization of one or more alkylene oxides. Further, the use of the Lewis acid catalyst during the polymerization reaction may reduce certain side reactions that lead to increased polydispersity and/or to increased acetal content in a final product.

The starter compound, also referred to as an initiator, has a low molecular weight such as less than 3,000 g/mol (e.g., less than 2,000 g/mol, less than 1,000 g/mol, less than 500 g/mol, less than 250 g/mol, etc.) and a nominal hydroxyl functionality at least 1. The initiator is any organic compound that is to be alkoxylated in the polymerization reaction. The initiator may contain as many as 8 or more hydroxyl groups. For example, the initiator may be a diol or triol. Mixtures of starter compounds/initiators may be used. The initiator will have a hydroxyl equivalent weight less than that of the polyether product, e.g., may have a hydroxyl equivalent weight of less than 333 g/mol equivalence, less than 300 g/mol equivalence, from 30 to 300 g/mol equivalence, from 30 to 250 g/mol equivalence, from 50 to 250 g/mol equivalence, etc. The starter compound may be linear or branched. The starter compound may include primary and/or secondary hydroxyl group(s).

Exemplary initiator compounds include, but are not limited to, at least one linear or branched alcohols such as secondary alcohols. Exemplary initiator compounds include, but are not limited to, ethylene glycols, diethylene glycols, triethylene glycols, propylene glycols, dipropylene glycols, tripropylene glycols, butane diols, hexane diols, octane diols, cyclohexane dimethanols, glycerins, trimethylolpropanes, trimethylolethanes, pentaerythritols, sorbitols, sucroses, octanols, nonanols, decanols, undecanols, dodecanols, tridecanals, tetradecanols, pentadecanols, dexadecanols, tridecyls: as well as alkoxylates (especially ethoxylates and/or propoxylates) of any of these that have a number average molecular weight less than that of the product of the polymerization (e.g., less than 3000 g/mol). The exemplary initiator compounds include variants thereof, e.g., such as 2-decanol, 3-decanol, 4-decanol, and 5-decanol. Other exemplary initiator compounds include trimethyl nonanol; methyl-, ethyl-, propyl-, butyl-, hexyl-, heptyl-, octyl-, nonyl-, and/or decyl-branched secondary alcohols. Other exemplary initiator compounds include secondary alcohols derived from hydrolysis of highly branched tripropylene, tetrapropylene, dibutylene, tributylene, and/or dihexene. In an exemplary embodiment, the starter compound may include a linear or branched secondary alcohol produced according to methods such as those described in U.S. Pat. No. 4,927,954. For example, the initiator compounds may include at least one detergent C8 to C16 range linear or branched secondary alcohol, such as 2,6,8-trimethyl-4-nonanol, 2-octanol, or linear or branched C11-C15 (e.g., C12-C14) secondary alcohol (or mixtures thereof).

The starter compound/initiator may be a low molecular weight polyether alcohol that has been formed using an alkylene oxide such as propylene oxide, ethylene oxide, and/or butylene oxide (e.g., which is polymerized with another starter compound/initiator). The starter compound may be a diol or triol. For example, the starter compound is an all propylene oxide based diol or triol having a hydroxyl functional based equivalent weight of less than 333 g/mol equivalence and/or less than 300 g/mol equivalence. In another example, the starter compound is an all ethylene oxide based diol or triol having a hydroxyl functional based equivalent weight of less than 333 g/mol equivalence and/or less than 300 g/mol equivalence When the Lewis acid catalyst is used the temperature of the reactor may be reduced at least 20° C. as compared to when the DMC catalyst is used. For example, the temperature for use of a DMC catalyst may be from 125° C. to 160° C. (e.g., during a time at which an alkylene oxide feed is gradually/slowly added to the reactor and after the time at which the starter compound is mixed with the DMC catalyst). The temperature for use of the Lewis acid catalyst may be from 25° C. to 115° C. and/or from 60° C. to 115° C. (e.g., during a time at which ethylene oxide is feed to the reactor to form an EO-capped alcohol). In exemplary embodiments, the control of the relative contribution of a mixture containing an active DMC catalyst and an active Lewis acid may enable the Lewis acid to dominate the addition of oxirane onto chain ends.

In an exemplary embodiment, when the polyether alcohol is derived from propylene oxide based initiator (e.g., a polyoxypropylene starter compound), during the polymerization process ethylene oxide may be added to the reaction mixture to form the polyether alcohol having a number average molecular weight of greater than the number average molecular weight of the initiator.

The polymerization reaction can be performed in any type of vessel that is suitable for the pressures and temperatures encountered. In a continuous or semi-continuous process the vessel may have one or more inlets through which the alkylene oxide and additional initiator compound may be introduced during the reaction. In a continuous process, the reactor vessel should contain at least one outlet through which a portion of the partially polymerized reaction mixture may be withdrawn. A tubular reactor that has single or multiple points for injecting the starting materials, a loop reactor, and a continuous stirred tank reactor (CSTR) are all suitable types of vessels for continuous or semi-continuous operations. An exemplary process is discussed in U.S. Patent Publication No. 2011/0105802.

The resultant polyether alcohol product may be further treated, e.g., in a flashing process and/or stripping process. For example, the polyether alcohol may be treated to reduce catalyst residues even though the catalyst residue may be retained in the product. Moisture may be removed by stripping the alcohol. The polyether alcohol derived from ethylene oxide, according to embodiments, may have a Lewis acid catalyst concentration (in ppm in the final polyoxypropylene alcohol) of from 50 ppm to 1000 ppm (e.g., 100 ppm to 500 ppm and/or 100 ppm to 250 ppm).

The polymerization reaction may be characterized by the "build ratio", which is defined as the ratio of the number average molecular weight of the polyether product to that of the initiator compound. This build ratio may be as high as 160, but is more commonly in the range of from 2.5 to about 65 and still more commonly in the range of from 2.5 to about 50. The build ratio is typically in the range of from about 2.5 to about 15, or from about 7 to about 11 when the polyether product has a hydroxyl equivalent weight of from 85 to 400.

Exemplary embodiments relate to preparing the polyether polyols using one or more of certain Lewis acid catalysts as polymerization catalysts that may achieve a lower acetal content in the resultant polyether polyols (e.g., less than 5.0 mol %, less than 4.0 mol %, less than 3.0 mol %, less than 1.5 mol %, less than 1.0 mol %, less than 0.8 mol %, less than 0.5 mol %, less than 0.2 mol % etc.), based on the total moles of carbon in the resultant polyol chains, while still producing high molecular weight polyols (e.g., poly-ethylene oxide polyols, poly-propylene oxide/ethylene oxide polyols, poly-ethylene oxide/butylene oxide polyols, etc.)

Exemplary embodiments related to preparing EO-capped polyether alcohols at a high yield, e.g., a yield of at least 50 wt %, at least 60 wt %, at least 70 wt %, at least 80 wt %, at least 90 wt %, at least 95 wt %, etc., based on a total weight of the resultant alcohol product.

Exemplary embodiments relate to using one or more of certain Lewis acid catalyst as polymerization catalyst, such that use of the Lewis acid catalyst may result in higher activation barriers to aldehyde formation, which is an undesired product, as compared to the activation barrier for forming the desired polyether polyol product or intermediate. As such the formation of the desired product or intermediate product may be favored during the polymerization process compared to the undesired products. For example, the activation barrier to aldehyde formation may be greater than 6.0 kcal/mol, greater than 7.0 kcal/mol, greater than 8.0 kcal/mol, and/or greater than 9.0 kcal/mol. The activation barrier to aldehyde formation may be less than 30 kcal/mol and/or less than 20 kcal/mol.

The alcohol ethoxylate surfactant or lubricant may be used in various applications. The alcohol ethoxylate surfactant or lubricant may be an additive in a blended composition for use in various applications. For example, the alcohol ethoxylate surfactant may be used to increase the cleaning and wetting properties of household cleaners, to enhance industrial and institutional cleaning product formulations, to contribute desired mechanical properties and/or storage stability to emulsion polymerization systems, in agricultural formulations, textile processing, paper manufacturing, oilfield operations, etc. The alcohol ethoxylate lubricant may be used in numerous industrial applications, e.g., as thickening agent, for lubrication, foam control, heat transfer, plasticizers, solvents, etc. The alcohol ethoxylate surfactant or lubricant may be a secondary alcohol ethoxylate surfactant or lubricant, e.g., prepared using a secondary alcohol has an initiator. The alcohol ethoxylates surfactant or lubricant may be linear or branched.

All parts and percentages are by weight unless otherwise indicated. All molecular weight values are based on number average molecular weight unless otherwise indicated.

Examples

Approximate properties, characters, parameters, etc., are provided below with respect to various working examples, comparative examples, and the materials used in the working and comparative examples.

Catalyst Synthesis

The general production for catalyst synthesis is as follows. Unless otherwise noted, all experimental procedures and manipulations of chemical substances are performed in a nitrogen-purged glove box or on a Schlenk line. All bulk reaction solvents (toluene, diethyl ether, hexane, tetrahydrofuran (THF)) are dried by passage through columns of alumina and Q5 reactive scavenger. All other solvents are purchased from Aldrich anhydrous grade and stored over activated 3 Å molecular sieves prior to use. NMR solvents (CDCl$_3$ and C$_6$D$_6$), obtained from Cambridge Isotope Laboratories, Inc., are dried over molecular sieves or, in the case of C$_6$D$_6$, dried using Na/K alloy. Further, 1-bromo-3,5-bis(trifluoromethyl)benzene, 1-bromo-2,4-difluoro-3-trifluoromethylbenzene, and 1-bromo-3,5-difluoro-4-trimethylbenzene are purchased from Oakwood Chemical. Also, 1-bromo-2,4,6-trifluoro-3-trifluoromethylbenzene, isopropylmagnesium chloride-lithium chloride (solution in THF), and boron trifluoride diethyletherate) are obtained from Sigma-Aldrich and used as received. Further, isopropylmagnesium chloride lithium chloride complex (solution in THF) is titrated before use using 1.00 M decanol in toluene with 1,10-phenanthroline as an indicator.

Multinuclear NMR spectra ($^1$H, $^{13}$C, $^{19}$F) are collected on one of the following instruments: Varian MR-400 or Varian VNMRS-500. The $^1$H and $^{13}$C NMR chemical shifts are referenced in parts per million relative to residual solvent peaks: $^1$H—7.15 ppm for C$_6$D$_6$, 7.25 ppm for CDCl$_3$; $^{13}$C—128.00 ppm for C$_6$D$_6$, and 77.00 ppm for CDCl$_3$. Boron-11 NMR chemical shifts are referenced externally to BF$_3$(Et$_2$O) (0 ppm), and $^{19}$F NMR chemical shifts are referenced externally to CFCl$_3$ (0 ppm). Sub-ambient reaction temperatures, except when dry ice or ice were the sole means of cooling, are measured using an Extech Instruments EasyView™ 10 Dual K model EA 10 thermometer with a fine JKEM sensor PTFE wire K 36INJ.

Catalyst 1 is (tris(3,5-bis(trifluoromethyl)phenyl)borane).
Catalyst 2, is the THF adduct of Catalyst 1.
Catalyst 1 and 2 are prepared according to the following Schematic 2:

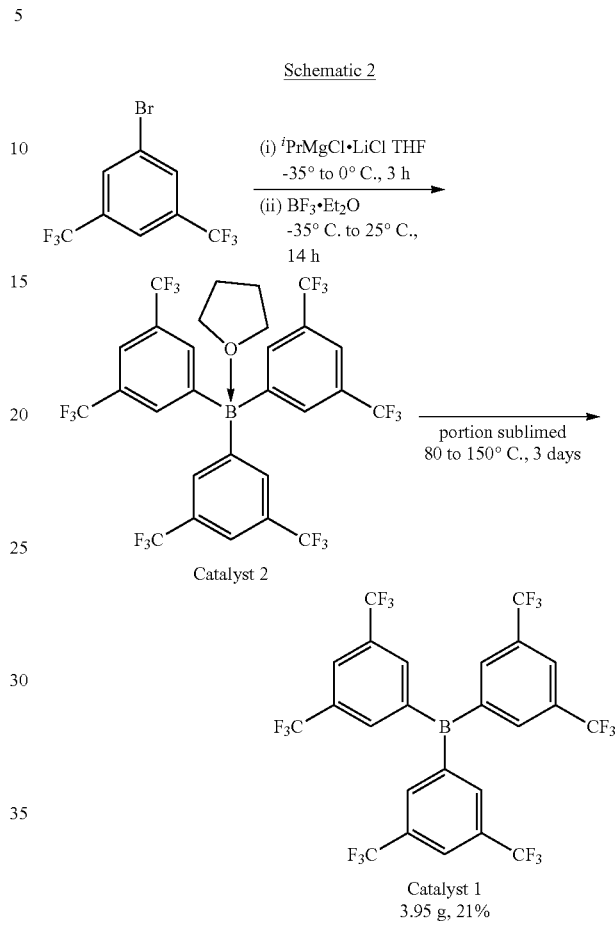

In particular, isopropylmagnesium chloride-lithium chloride (70.8 mL, 87.0 mmol, 1.23 M solution in THF) is added to a solution of 1-bromo-3,5-bis(trifluoromethyl)benzene (25.5 g, 87.0 mmol) in THF (250 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (4.26 mL, 29.0 mmol) is added while maintaining the reaction mixture at a temperature range of between −35° C. to −25° C. The reaction mixture is allowed to warm to room temperature while it is stirred overnight. The resultant $^{19}$F NMR spectra of the reaction mixture shows a major peak (95%) at δ −63.2 and a minor peak (5%) at δ −63.7 corresponding to 1-bromo-3,5-bis(trifluoromethyl)benzene. Next, the THF is removed from the reaction mixture under reduced pressure. The residue is extracted with toluene and filtered using several PTFE frits because the very fine precipitate may be difficult to filter. The volatiles are removed under reduced pressure to give a very viscous oil. A portion of the product (about ⅔ to ¾) is put in a sublimator and sublimed (by starting at 80° C. and gradually increasing the temperature to 150° C. over several days in an oil bath under ≤1 mtorr vacuum) to give 3.95 grams (6.07 mmol, 21%) of white solid on the sublimator finger. Small crystals may also be present. This material is characterized by multinuclear NMR spectroscopy as Catalyst 1. Additional, less pure, product is scraped out of the top portion of the sublimator body, in an amount of 2.01 grams. The less pure material, which by NMR is characterized as a 2:1 mixture of borane to THF, is dissolved in THF, filtered, and the volatiles are removed under reduced pressure. This material is characterized by multinuclear NMR spectroscopy as Catalyst 2 (2.00 g, 2.77 mmol, 9.5%) Total yield: 6.07 mmol Catalyst 1 and 2.77 mmol Catalyst 2 (30% overall yield).

Catalyst 3 is the THF adduct of tris(2,4-difluoro-3-(trifluoromethyl)phenyl)borane and is prepared according to Schematic 3:

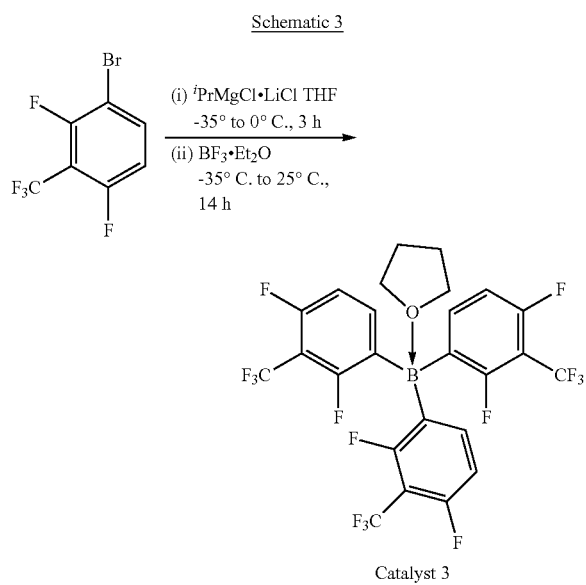

Catalyst 3

In particular, isopropylmagnesium chloride-lithium chloride (15.6 mL, 19.2 mmol, 1.23 M solution in THF) is added to a solution of 1-bromo-2,4-difluoro-3-trifluoromethylbenzene (5.00 g, 19.2 mmol) in THF (100 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (0.79 mL, 6.4 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(2,4-difluoro-3-(trifluoromethyl)phenyl)borane.

Catalyst 4 is the THF adduct of tris(3,5-difluoro-4-(trifluoromethyl)phenyl)borane and is prepared according to Schematic 4:

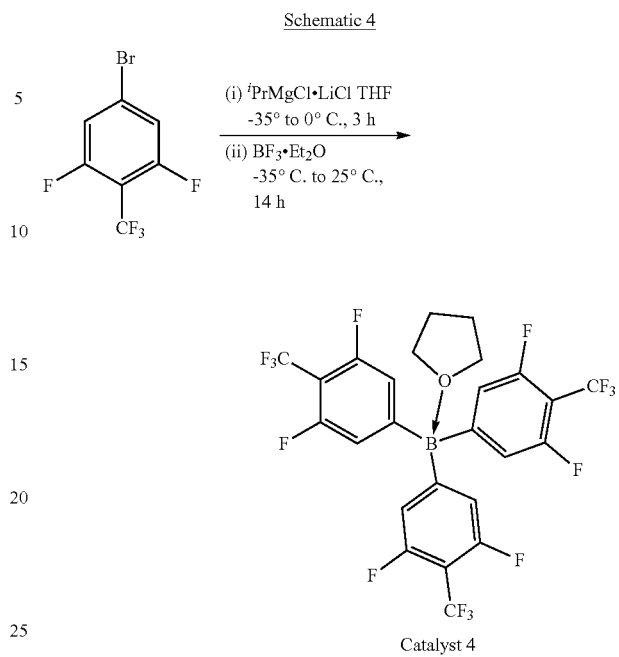

Catalyst 4

In particular, isopropylmagnesium chloride-lithium chloride (31.1 mL, 38.3 mmol, 1.23 M solution in THF) is added to a solution of 1-bromo-3,5-difluoro-4-trifluoromethylbenzene (10.0 g, 38.3 mmol) in THF (150 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (1.58 mL, 12.8 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(3,5-difluoro-4-(trifluoromethyl)phenyl)borane.

Catalyst 5 is the THF adduct of tris(2,4,6-trifluoro-3-(trifluoromethyl)phenyl)borane and is prepared according to Schematic 5:

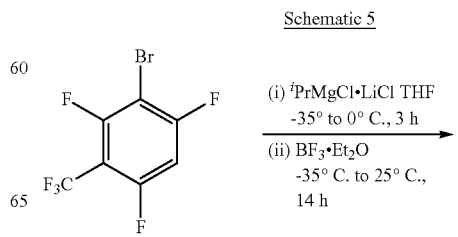

-continued

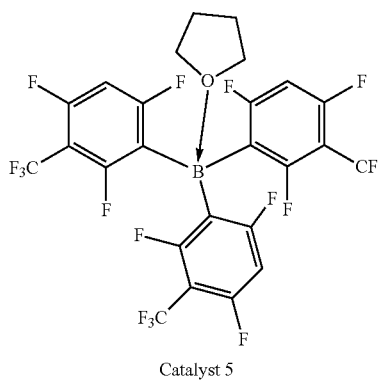

Catalyst 5

In particular, isopropylmagnesium chloride-lithium chloride (5.9 mL, 7.3 mmol, 1.23 M solution in THF) is added to a solution of 1-bromo-2,4,6-trifluoro-3-trifluoromethyl-benzene (2.00 g, 7.17 mmol) in THF (50 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (0.30 mL, 2.4 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(2,4,6-trifluoro-3-(trifluoromethyl)phenyl)borane.

Catalyst A is Tris(pentafluorophenyl)borane, also referred to as FAB, available from (available from Boulder Scientific).

Catalyst B is Boron Trifluoride Diethyl Etherate, also referred to as $BF_3$ (available from Sigma Aldrich).

Catalyst C is Potassium Hydroxide obtained with 10% water content, also referred to as KOH (available from Sigma Aldrich)

Preparation of Alcohols

For preparing the alcohols, the following materials are principally used:

| | |
|---|---|
| Starter 1 | A starter compound that is 2,6,8-trimethyl-4-nonanol, also referred to as TMN (available from Sigma-Aldrich Corporation). |
| Solvent | A glycol diether that has no hydroxyl functionality (available from The Dow Chemical Company as PROGLYDE ™ DMM). |
| Additive | An acidifying agent that includes phosphoric acid. |
| Magnesium Silicate | A salt (available from Sigma-Aldrich Corporation). |

In particular, the following reaction may be carried out in a continuous flow reactor using Catalysts 1 to 5 as discussed above. The reactions may be carried out in a manner shown below in exemplary Schematic 6, and in view of the conditions provided in Table 1:

Schematic 6

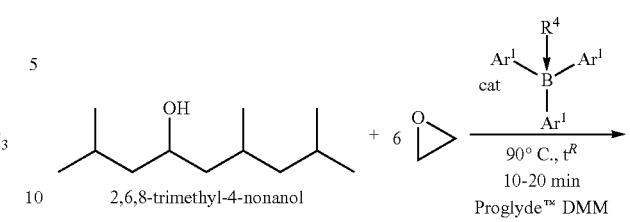

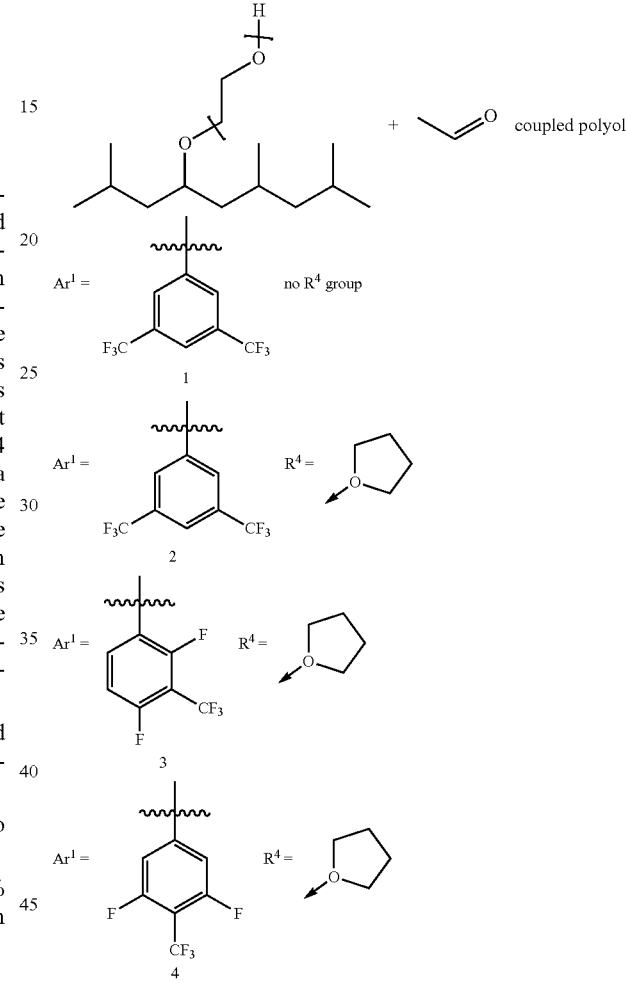

The alcohols of Working Examples 1 to 5 and Comparative Examples B and C may be prepared using Starter 1 as the initiator, ethylene oxide (EO) as the monomer, and the Solvent according to the conditions outlined in Table 1, below. Referring to Table 1, the EO binding enthalpy, and activation barrier to aldehyde are determined according to the computational methods discussed below.

TABLE 1

| | Catalyst | Catalyst Con. (ppm) | Time (Min) | Temp (° C.) | EO binding enthalpy (kcal/mol) | Activation barrier to aldehyde (kcal/mol) |
|---|---|---|---|---|---|---|
| Ex. A | — | — | 10 | 90 | n/a | n/a |
| Ex. B | A | 1000 | 10 | 90 | −6.0 | 5.3 |
| Ex. C | | | 20 | | | |

TABLE 1-continued

| Catalyst | Catalyst Con. (ppm) | Time (Min) | Temp (° C.) | EO binding enthalpy (kcal/mol) | Activation barrier to aldehyde (kcal/mol) |
|---|---|---|---|---|---|
| Ex. 1 | 1 | 1000 | 10 | 90 | −3.7 | 8.7 |
| Ex. 2 | | | 20 | | | |
| Ex. 3 | 2 | 1000 | 10 | 90 | | |
| Ex. 4 | 3 | 1000 | 10 | 90 | −5.7 | 6.2 |
| Ex. 5 | 4 | 1000 | 10 | 90 | −6.8 | 9.9 |

Comparative Example A is a negative control that may be run without catalyst. This example may be carried out by mixing the initiator and ethylene oxide in the tubular reactor at 90° C. for 10 min.

The alcohol samples for Working Examples 1 to 5 and Comparative Examples B and C, may be prepared in a continuous flow reactor that is a microreactor available from Vapourtec Inc. For the examples, neat EO monomer is fed to a pump via a pressure cylinder at 50 psig. A solvent reservoir containing the Solvent is connected to another pump. A 2 mL injection loop is utilized to introduce a solution of the specified catalyst and initiator (as 60 wt % of P390 in dipropylene glycol dimethyl ether) into the system. By controlling the flow rate, the catalyst and starter are introduced into the flow system at a defined rate. The EO monomer and initiator-catalyst-Solvent solution are combined at a mixing unit and fed into a 2 mL stainless steel coiled reactor. A back pressure regulator set at 250 psig is used to control the system pressure and assist the EO to remain in a liquid phase. The continuous pressure reactor is charged with 0.1 mL/min of the initiator-catalyst-Solvent mixture. The ethylene oxide may be fed to the reactor at a constant feed rate of 0.1 mL/min. Once the initiator-catalyst-Solvent mixture is introduced into the sample loop, the first 5.13 mL of the product mixture is diverted to a scrubber consisting of 3 wt % aqueous potassium hydroxide. The next 3.04 mL of product mixture may be collected and analyzed by MALDI spectrometry.

The Temperature in Table 1 is the temperature in the reactor. The Time is residence time, which is defined as follows:

$$\text{residence time} = \frac{\text{reactor volume}}{\left(\begin{array}{c}\text{flow rate of pump } A + \\ \text{flow rate of pump } B\end{array}\right)}$$

When the flow rates of pumps A and B are 0.1 mL/min, $$\text{residence time} = \frac{2 \text{ mL}}{(0.1 + 0.1) \text{ mL/min}} = 10 \text{ min}$$

When the flow rates of pumps A and B are 0.05 mL/min, $$\text{residence time} = \frac{2 \text{ mL}}{(0.05 + 0.05) \text{ mL/min}} = 20 \text{ min}$$

The number-average molecular weight (Mn) achieved in the polymerization reaction may depend on the amount of volatile side-products (e.g. acetaldehyde) formed. For example, higher levels of volatile side-products may result in a Mn that is significantly lower than the theoretical Mn. Conversely, low levels of volatile side-products may help achieve a Mn that is close to the theoretical Mn. It may be desirable to achieve a Mn that is close to the theoretical Mn.

The PDI is defined as the ratio of the weight-average molecular weight (Mw) to the number-average molecular weight (Mn). The PDI may represent a measure of the extent of acetal coupling, as this reaction may effectively double the molecular weight. Accordingly, a comparison of the PDI at similar Mn values may provide a measure of the selectivity of a catalyst for alkoxylation (intended reaction) versus isomerization and acetalization. Lower PDI may be preferable for higher chemoselectivity.

The EO binding enthalpy is calculated relative to a resting state consisting of the free catalyst (where $R^4$ is not present) and EO. Favorable binding (higher negative values, for example greater than −3.0 kcal/mol, greater than −5.0 kcal/mol, etc) is preferable for higher activity. Referring to Table 1, it is seen that calculations on Catalysts 1 to 4 provide a favorable EO binding enthalpy such that favorable activity is realized. Another measure of activity is the ring opening barrier shown below. Lower ring opening barriers are preferable for higher activity.

The activation barrier to aldehydes determines the amount of aldehyde and acetal formed, as shown in FIG. 1. Higher activation barriers are preferable for lower levels of aldehyde and subsequent acetal formation.

Referring to Working Examples 1 to 5 and Comparative Examples B and C, it is found that the activation barrier to undesired products (in comparison to the activation barrier for the desired EO content polyether polyol) is significantly higher for Catalysts 1 to 4 compared to Catalyst A. As such, it is unexpectedly found that the structures of Catalysts 1 to 4 may allow for increased yield of the desired product, as compared to Catalyst A.

Additional, Working Example 6 and Comparative Example D, E, and F are carried out in a semi-batch process using Starter 1 and EO, using the Catalysts 2, A, B, and C.

Referring to Table 2, Theo Mn refers to the theoretical number average molecular weight defined as:

$$Mn = \frac{\text{Mass of Initiator} + \text{Mass of Monomer }(s)}{\text{Moles of Initiator}}$$

Referring to Table 2, GPC Mn refers to the number average molecular weight measured by GPC, Dioxane refers to the amount of 1,4-dioxane in the product, Unreacted SM refers to the percentage of peak area corresponding to Starter 1 in the GPC chromatogram, and Dimer refers to the percentage of peak area corresponding to a molecular weight which is twice the GPC $M_n$. The GPC Mn, Unreacted SM, Dioxane, and Dimer are determined according to the analytical methods discussed below.

TABLE 2

| | Init | Mon | Catalyst | Temp (° C.) | Theo Mn | GPC Mn | Unreacted SM | Dioxane (ppm) | Dimer |
|---|---|---|---|---|---|---|---|---|---|
| Ex. D | Starter 1 | EO | B | 50 | 450 | 562 | 5.9 | 16796 | — |
| Ex. E | Starter 1 | EO | C | 120 | 362 | 1034 | 16.6 | 307 | — |
| Ex. F | Starter 1 | EO | A | 50 | 443 | 431 | 5.2 | 2629 | 14 |

TABLE 2-continued

| | Init | Mon | Cata-lyst | Temp (° C.) | Theo Mn | GPC Mn | Un-reacted SM | Di-oxane (ppm) | Dimer |
|---|---|---|---|---|---|---|---|---|---|
| Ex. 6 | Starter 1 | EO | 2 | 50 | 522 | 415 | 4.7 | 687 | 8 |

For the semi-batch process, a semi-batch pressure reactor configuration equipped with a pneumatically driven impeller, thermocouple, cooling water coils, a dip tube (¼" OD) that is connected to a nitrogen line, monomer feed line and a vent using a four-way Swagelok fitting, and an aluminum heating block, is used. Starter 1 was dried by distillation to <100 ppm water and stored under nitrogen to be used for Comparative Example F and Working Example 6.

For Comparative Example D, a 2 L pressure reactor was charged with 101.36 g of Starter 1. The reactor was sealed, pressure checked, purged with nitrogen, then a headspace port was opened and 0.65 g of Catalyst B was added using a syringe. The system was sealed and heated to 50° C. for the addition of 143.6 g of EO at an addition rate of 1 g/min. After holding for one hour at 50° C., the mixture was cooled to 30° C. and collected (242.4 g, 99%). The clear solution was mixed with 10.0 g of Magnesium Silicate and 2.06 g of water, and vacuum filtered to generate 218.81 g of clear filtrate.

For Comparative Example E, a 250-mL round bottom flask was charged with 136.32 g of Starter 1, 1.30 g of Catalyst C, and 0.5 mL of water. The solution was heated under a vacuum of 8 torr to a pot temperature of up to 111° C. to collect 17.23 g of distillate at a head temperature of up to 96° C. The base content was measured at 1.04 wt % (as Catalyst C). A 2 L pressure reactor was charged with 89.88 g of this solution, and the reactor was sealed, pressure checked, purged with nitrogen, and then heated to 120° C. for the addition of 128.6 g of EO at an addition rate of 2 g/min. The reaction product was held at 120° C. for one hour to a constant pressure, then cooled to 80° C. to unload 213.45 g. The warm liquid product was mixed with 10.0 g of Magnesium Silicate and 2.0 g of water, and vacuum filtered to afford 186.84 g of a light brown product which solidified upon cooling.

For Comparative Example F, Starter 1 (51.35 g) was transferred via syringe to a dry reactor under positive nitrogen pressure and the reactor was heated to 50 C with stirring. Catalyst A (72.6 mg) was dissolved in 1 mL of dry THF and transferred to the reactor via syringe. Three cycles of pad/de-pad were used to ensure an inert environment in the reactor after catalyst addition. Ethylene oxide (72.751 g) was fed to the reactor subsurface at 0.75 g/min. Upon completion of oxide feed, the reactor was blocked in and allowed to digest until a constant pressure of <0.3 psi change over 10 minutes was observed. The reactor was subsequently vented and the product was collected (111.09 g, 89.5%).

For Working Example 6, Starter 1 (52.2 g) was transferred via syringe to a dry reactor under positive nitrogen pressure and the reactor was heated to 50 C with stirring. Catalyst 2 (71.8 mg) was dissolved in 1 mL dry THF and transferred to the reactor via syringe. Three cycles of pad/de-pad were used to ensure an inert environment in the reactor after catalyst addition. Ethylene oxide (74.4 g) was fed to the reactor subsurface at 0.75 g/min. Upon completion of oxide feed, the reactor was blocked in and allowed to digest until a constant pressure of <0.3 psi change over 10 minutes was observed. The reactor was subsequently vented and the product was collected (107.7 g, 84.0%).

For Working Example 7, Starter 1 (52 g) was transferred via syringe to a dry reactor under positive nitrogen pressure and the reactor was heated to 50 C with stirring. Catalyst 3 (70 mg) was dissolved in 1 mL dry THF and transferred to the reactor via syringe. Three cycles of pad/de-pad were used to ensure an inert environment in the reactor after catalyst addition. Ethylene oxide (75 g) was fed to the reactor subsurface at 0.75 g/min. Upon completion of oxide feed, the reactor was blocked in and allowed to digest until a constant pressure of <0.3 psi change over 10 minutes was observed. The reactor was subsequently vented and the product was collected.

For Working Example 8, Starter 1 (52 g) was transferred via syringe to a dry reactor under positive nitrogen pressure and the reactor was heated to 50 C with stirring. Catalyst 4 (70 mg) was dissolved in 1 mL dry THF and transferred to the reactor via syringe. Three cycles of pad/de-pad were used to ensure an inert environment in the reactor after catalyst addition. Ethylene oxide (75 g) was fed to the reactor subsurface at 0.75 g/min. Upon completion of oxide feed, the reactor was blocked in and allowed to digest until a constant pressure of <0.3 psi change over 10 minutes was observed. The reactor was subsequently vented and the product was collected.

For Working Example 9, Starter 1 (52 g) was transferred via syringe to a dry reactor under positive nitrogen pressure and the reactor was heated to 50 C with stirring. Catalyst 5 (70 mg) was dissolved in 1 mL dry THF and transferred to the reactor via syringe. Three cycles of pad/de-pad were used to ensure an inert environment in the reactor after catalyst addition. Ethylene oxide (75 g) was fed to the reactor subsurface at 0.75 g/min. Upon completion of oxide feed, the reactor was blocked in and allowed to digest until a constant pressure of <0.3 psi change over 10 minutes was observed. The reactor was subsequently vented and the product was collected.

Referring to Table 2, it is seen that the residual starting material is less when Catalyst 2 is used, as compared to Catalyst C. As a result, the actual number average molecular weight as measured by GPC is significantly closer to the theoretical number average molecular weight for Working Example 6, as compared to Comparative Example E. The dioxane content of the product formed with Catalyst 2 is significantly reduced, as compared to the dioxane contents of the products formed with Catalysts A and B. The area of the dimer peak in Working Example 6 is less than Comparative Example F.

A process for the preparation of a polyether polyol may be carried out in a continuous or semi-batch process using a sequential dual catalyst process, similar to International Publication No. WO 2016/064698, which is incorporated by reference.

The analytical methods used with respect to the examples are described below:

Determination of $M_n$ for semibatch products: Gel Permeation Chromatography (GPC) analysis is used for determination of number average molecular weight (Mn), which is carried out at a flow rate of 1.0 mL/min using four PLgel organic GPC columns connected in series (3 μm, Agilent Inc.) and tetrahydrofuran as eluent. The column temperature is 40° C. VORANOL™ CP 6001, VORANOL™ 210, 230-660, and 230-056N are used as standards.

Determination of residual starting material and dioxane content by GC-FID-MSD: Samples were prepared by dilution of the polyol samples 1:4 by weight with dichlorobenzene. A gas chromatography method with simultaneous flame ionization detection and mass selective detection (GC-FID-MSD) was developed. The method uses an Agilent HP-5 (30 m×0.32 mm×0.25 μm) employed in a 7890A Agilent GC with standard FID and an Agilent 5975C inert MSD with Triple-Axis Detector (350° C. capable). The column effluent was split between FID and MSD. The vacuum flow through the MSD is controlled via a restrictor line (0.45 m×0.1 mm×0 μm) to give a flow of 0.75 mL/min. The rest of the effluent goes to the FID unrestricted at 1.75 mL/min. Quantitation values were based on the FID chromatogram and identification of peaks were derived from the MS spectra of component and matched to the NIST MSD library.

Computational Methodology for determination of binding enthalpy and activation barrier to aldehyde: The structures of species in ground and transition states are optimized using Density Functional Theory (DFT) at B3LYP/6-31g** level. The effect of dielectric medium is included by using conductor like polarizable continuum model (CPCM), where diethylether ($\varepsilon$=4.2) is used as the medium of choice. The vibrational analysis on the ground state geometries is performed and the lack of imaginary frequencies is used to ascertain the minima in the potential energy surface (PES). On the other hand, the same analysis on the transition state geometries indicated one imaginary frequency. In the latter case, the GaussView program is used to visualize the vibrational mode with imaginary frequency in order to ensure that the atoms moved along the desired reaction coordinate. For both ground-state and transition state geometries, the vibrational analysis is used to compute the enthalpy ($H_{298}$) at 298 K by augmenting zero point energy to the electronic energy. For both ground state and transition state, various conformations were explored and the enthalpy of the lowest conformation was used to calculate binding and the barrier height for aldehyde formation. These calculations were performed using G09 suit of programs.

Computational determination of free (or accessible) volume: Once the optimized geometry of free catalysts (where the catalyst is not bound to the optional $R^4$ Lewis base) or coordinated complexes (where a catalyst is bound to the optional $R^4$ Lewis base) are obtained using the above method, a sphere of radius 3.0 Å is placed around the B atom (the volume of this sphere is denoted as V1). This is followed by placing spheres on other atoms; the radii of these spheres are chosen to be the van der Waals radii of respective atoms. The volume of the sphere centered on B which is occluded by spheres on other atoms is computed using a Monte Carlo integration technique. The occluded volume is represented as V2. The free volume (FV) is calculated using the following equation:

$$FV=1-(V2/V1)$$

The FV descriptor varies between 0 and 1. This technique is implemented using Pipeline Pilot tool kit. This procedure is used in literature to understand bond dissociation trends.

The invention claimed is:

1. A method of producing an alcohol ethoxylate surfactant or lubricant, the method comprising:
reacting a low molecular weight initiator with ethylene oxide in the presence of a polymerization catalyst, the low molecular weight initiator having a nominal hydroxyl functionality of at least 1, and the polymerization catalyst being a Lewis acid catalyst having the general formula $M(R^1)_1(R^2)_1(R^3)_1(R^4)_1$, whereas M is boron, aluminum, indium, bismuth or erbium, $R^1$, $R^2$ and $R^3$ each includes a same fluoroalkyl-substituted phenyl group, and $R^4$ includes a functional group or functional polymer group; and
forming the alcohol ethoxylate surfactant or lubricant having a number average molecular weight of greater than the number average molecular weight of the low molecular weight initiator in the presence of the Lewis acid catalyst.

2. The method as claimed in claim 1, wherein the Lewis acid catalyst has the general formula $M(R^1)_1(R^2)_1(R^3)_1(R^4)_1$, whereas M is boron, and each of $R^1$, $R^2$, and $R^3$ is a 3,4- or 3,5-bis(fluoroalkyl)-substituted phenyl group.

3. The method as claimed in claim 1, wherein the Lewis acid catalyst has the general formula $M(R^1)_1(R^2)_1(R^3)_1(R^4)_1$, whereas M is boron, and each of $R^1$, $R^2$, and $R^3$ is a fluoro/chloro-fluoroalkyl-substituted phenyl group, difluoro/chloro-fluoroalkyl-substituted phenyl group, trifluoro/chloro-fluoroalkyl-substituted phenyl group, or tetrafluoro/chloro-fluoroalkyl-substituted phenyl group.

4. The method as claimed in claim 1, wherein $R^4$ is a cyclic ether having 3-10 carbon atoms.

5. The method as claimed in claim 1, wherein $R^4$ is a ketone having 3-10 carbon atoms.

6. The method as claimed in claim 1, wherein the low molecular weight initiator is a secondary alcohol and the alcohol ethoxylate surfactant or lubricant is a secondary alcohol ethoxylate surfactant or lubricant.

7. The method as claimed in claim 1, wherein the low molecular weight initiator is a secondary alcohol having a number average molecular weight of less than 3,000 g/mol and the alcohol ethoxylate surfactant or lubricant is a secondary alcohol ethoxylate surfactant or lubricant.

* * * * *